United States Patent [19]
Angelchik

[11] Patent Number: 5,006,106
[45] Date of Patent: Apr. 9, 1991

[54] APPARATUS AND METHOD FOR LAPAROSCOPIC IMPLANTATION OF ANTI-REFLUX PROSTHESIS

[76] Inventor: Jean P. Angelchik, 522 W. Northview, Phoenix, Ariz. 85021

[21] Appl. No.: 594,011

[22] Filed: Oct. 9, 1990

[51] Int. Cl.⁵ .................. A61F 2/00; A61F 13/00; A61B 19/00
[52] U.S. Cl. ................................. 600/37; 623/11; 128/898; 128/899
[58] Field of Search .................. 600/37; 623/11; 128/898, 899; 606/157, 158, 201, 202

[56] References Cited

U.S. PATENT DOCUMENTS

| | | | |
|---|---|---|---|
| 3,831,583 | 8/1974 | Edmunds, Jr. et al. | 606/202 X |
| 3,875,928 | 4/1975 | Angelchik | 600/37 |
| 4,271,827 | 6/1981 | Angelchik | 600/37 |
| 4,271,828 | 6/1981 | Angelchik | 600/37 |
| 4,796,603 | 1/1989 | Dahlke et al. | 128/899 |

*Primary Examiner*—Ronald Frinks
*Attorney, Agent, or Firm*—William H. Drummond

[57] ABSTRACT

A prosthesis and method for treating gastro esophagus reflux. The prosthesis is a normal C-shaped cushion member, the inside diameter of which is generally larger than the normal outside diameter of the distal esophagus. The C-shaped member is temporarily deformable to a shape adapted for inserting the member into the abdominal cavity through a laparoscopic portal. A shaping spring normally maintains the cushion member in the C-shape and is deformable to permit inserting the C-shaped member through the portal.

An optical viewing laparscope is inserted through the abdominal wall of the torso. The prosthesis is temporarily deformed and inserted through a laparoscopic portal in the torso wall. The prosthesis is then positioned around the distal esophagus adjacent the diaphragm.

2 Claims, 5 Drawing Sheets

APPARATUS AND METHOD FOR LAPAROSCOPIC IMPLANTATION OF ANTI-REFLUX PROSTHESIS

This invention relates to a surgical prosthesis and method of use.

More particularly, the invention concerns a laparoscopically implantable prosthesis for controlling gastro esophageal reflux.

According to another embodiment, the invention relates to a laparoscopic method for preventing, reducing and treating reflux of gastric contents into the esophagus.

Methods and apparatus for the prevention of gastro esophageal reflux are described in my prior U.S. Pat. Nos. 3,875,928, issued April 8, 1975, and 4,271,828, issued June 9, 1981. An alternate method, generally employing a similar prosthesis is also described in my prior U.S. Pat. No. 4,271,827, issued June 9, 1981.

While such methods and prostheses have proven to be effective and safe, they do require invasive surgery. It would, therefore, be desirable to provide prostheses and methods for implantation thereof by laparoscopic techniques which would avoid such invasive surgery.

Accordingly, a principal object of the present invention is to provide a prosthesis for preventing gastro esophageal reflux which prosthesis is specially constructed for implantation through a laparoscopic portal.

Another principal object of the invention is to provide a non-invasive laparoscopic method for implantation of such an anti reflux prostheses.

These, other and further objects and advantages of the invention, will be apparent to those skilled in the art from the following detailed description thereof, taken in conjunction with the drawings in which.

Figure 7:
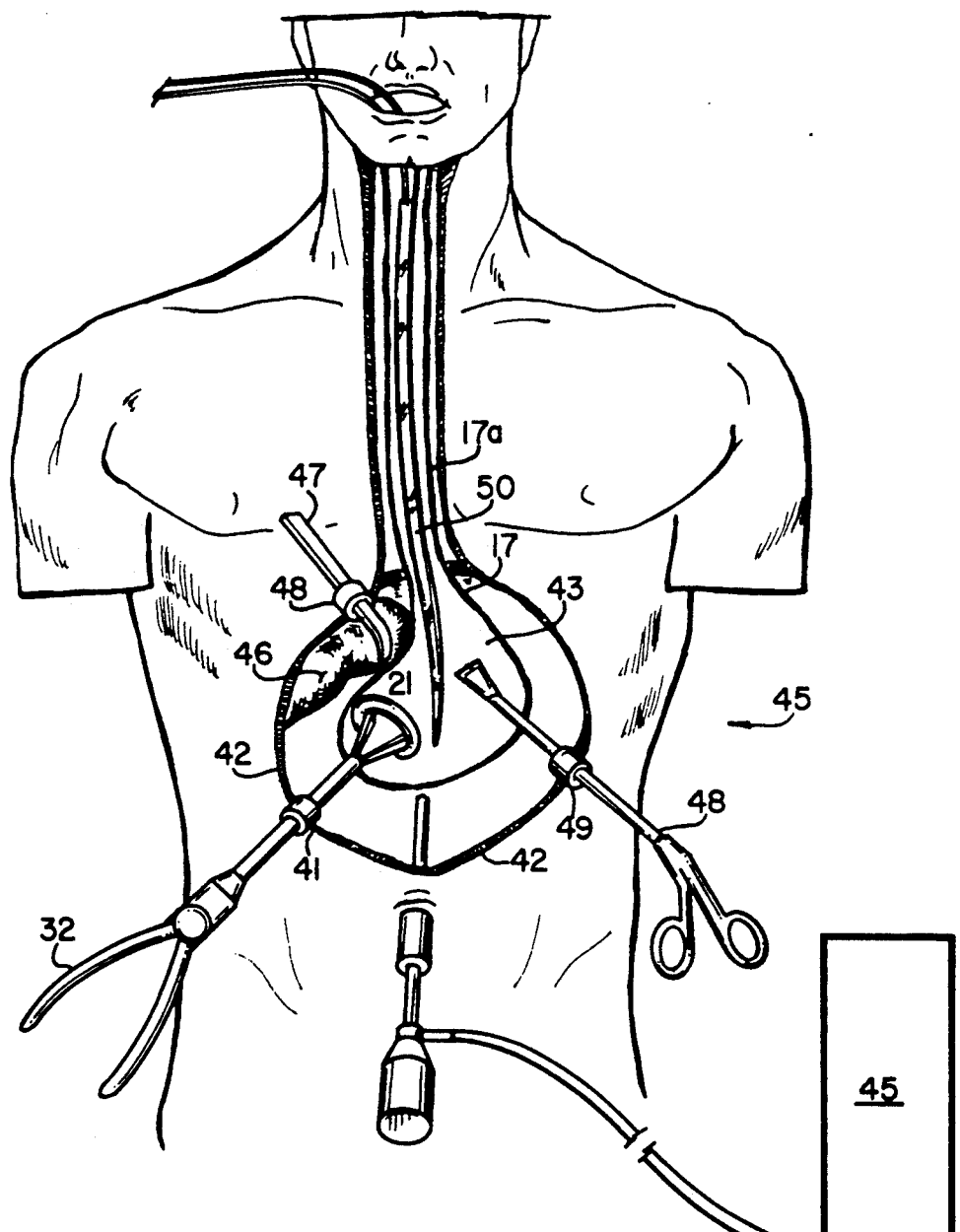
Figure 8:
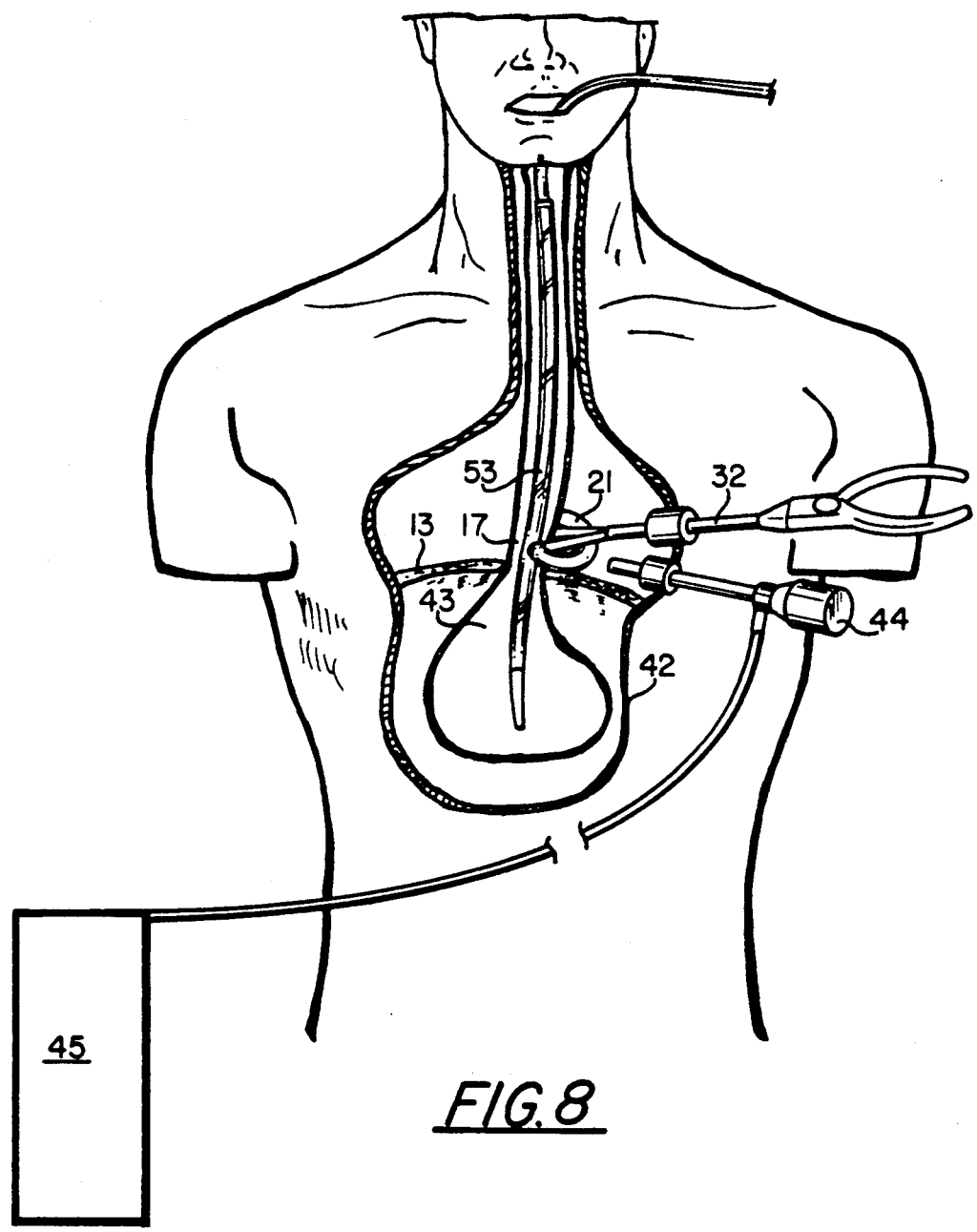

FIG. 7 is a cut-away view of the abdominal cavity, showing the laparoscopic instrumentation employed and generally depicting the method of implantation, according to the presently preferred embodiment of the invention; and FIG. 8 is a cut-away view of the thoracic cavity, depicting an alternate embodiment of the method of the invention in which an anti-reflux prosthesis is positioned around the distal esophagus above the diaphragm.

Figure 9:
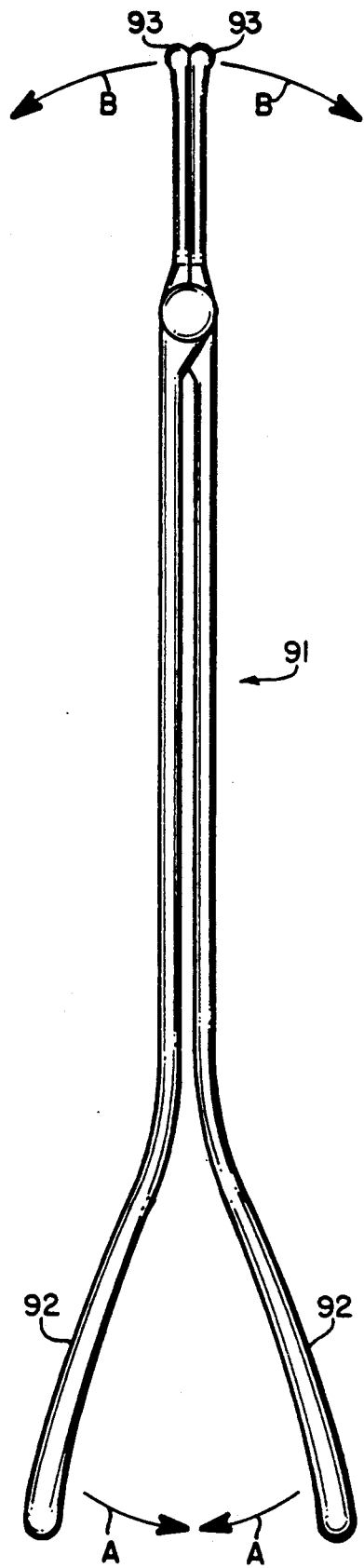

FIG. 9 depicts implantation forceps for suitable use in practicing the method of the invention.

Figure 10:
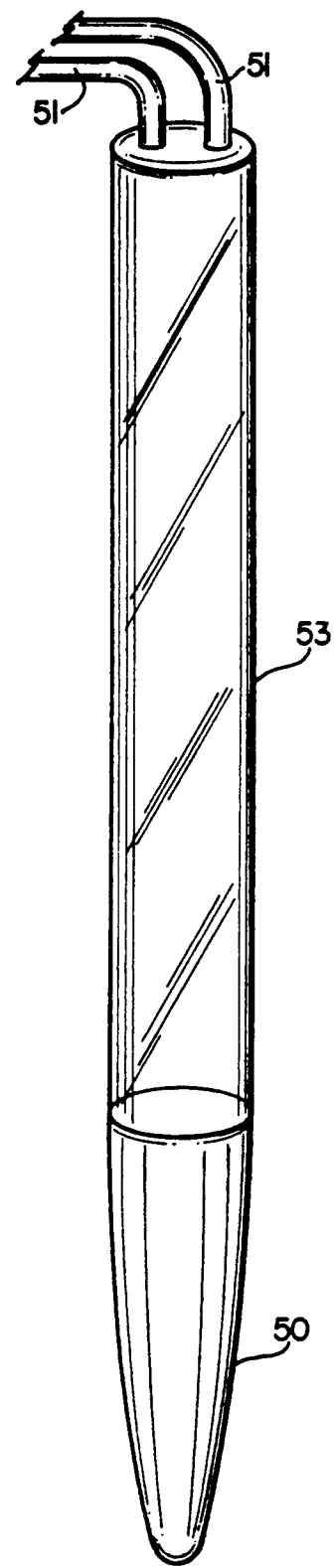

FIG. 10 depicts an illuminating bougie which is preferably employed in the practice of the methods of my invention to facilitate visualization of the laparoscopic implantation procedure by directing light through the walls of the distal esophagus.

Briefly, in accordance with one embodiment of my invention, I provide a laparoscopically implantable prosthesis for controlling gastro esophageal reflux. The prosthesis comprises a normally generally C-shaped cushion member, the inside diameter of which is generally larger than corresponds to the normal outside diameter of the distal esophagus. The C-shaped member is temporarily deformable to a shape adapted for inserting the member into the torso (abdominal or thoracic) cavity through a laparoscopic portal. Shaping spring means are formed with the cushion member to normally maintain the cushion member in the C-shape, these spring means being temporarily deformable with the C-shape member to the shape which is insertable through the laparoscopic portal.

Further, briefly, I provide a method for treating gastro esophageal reflux. This method includes the steps of inserting a laparoscopic portal through the torso wall into a torso cavity, inserting an optical viewing laparoscope through the abdominal wall and positioning the scope to view the distal esophagus, applying force to temporarily deform the prosthesis described above for insertion through the laparoscopic portal, inserting the temporarily deformed prosthesis through the portal, positioning the prosthesis adjacent the diaphragm and releasing the deforming force to cause the prosthesis to autogenously assume its normal C-shape in operative position around the distal esophagus.

According to another embodiment, the method of the invention includes the steps of inserting a laparoscopic portal through the wall into the torso thoracic cavity, inserting an optical viewing laparoscope through the thoracic wall and positioning the scope to view distal esophagus above the diaphragm, applying force to temporarily deform the prosthesis for insertion through the laparoscopic portal, inserting the temporarily deformed prosthesis through the portal, positioning the prosthesis around the distal esophagus above the diaphragm and releasing the deforming force to cause the prosthesis to autogenously assume its normal C-shape in operative position around the esophagus.

The drawings are presented for the purpose of illustrating the practice of my invention, so as to enable those skilled in the art to understand and practice it, but are not intended as limitations upon the scope of the invention. Further, the drawings illustrate the best mode which I presently contemplate for carrying out my invention, again without intending to limit the scope thereof. In these drawings, like reference characters depict the same elements in the several views.

Figure 1:
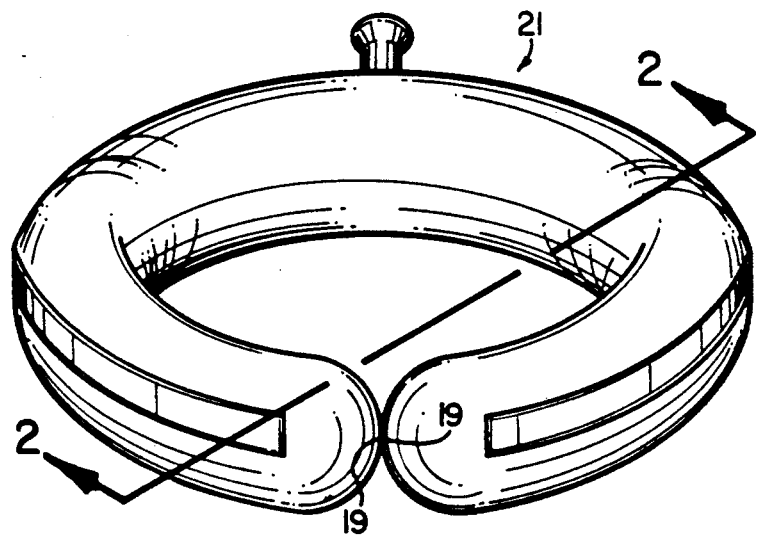
FIG. 1 is a perspective view of a prosthesis constructed in accordance with a presently preferred embodiment of the invention.
Figure 2:
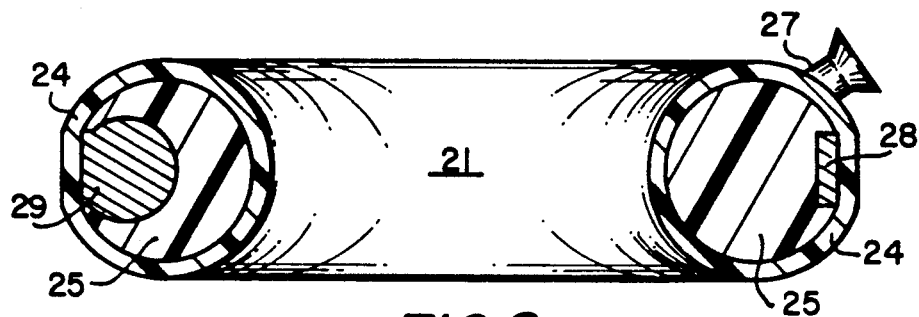
FIG. 2 is a sectional view of the prosthesis of FIG. 1, taken along section line 2—2 thereof.
Figure 3:
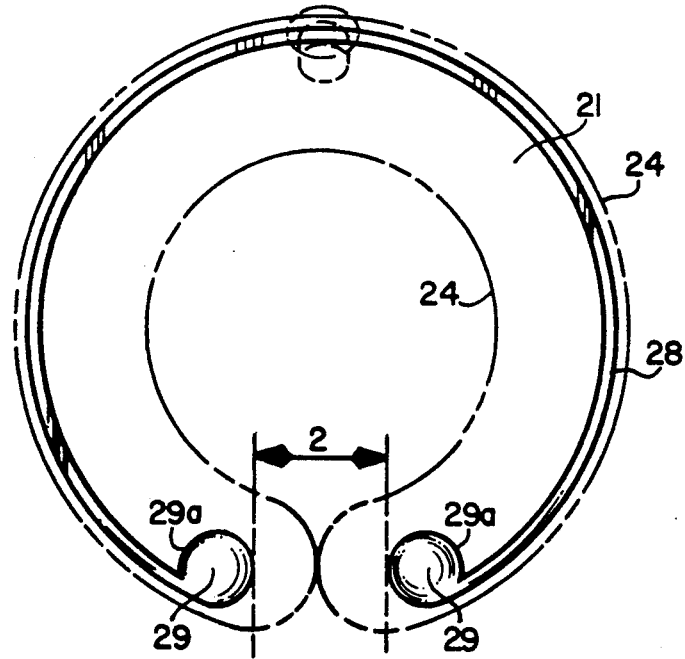
FIG. 3 is a plan view of the prosthesis of FIGS. 1-2.
Figure 4:
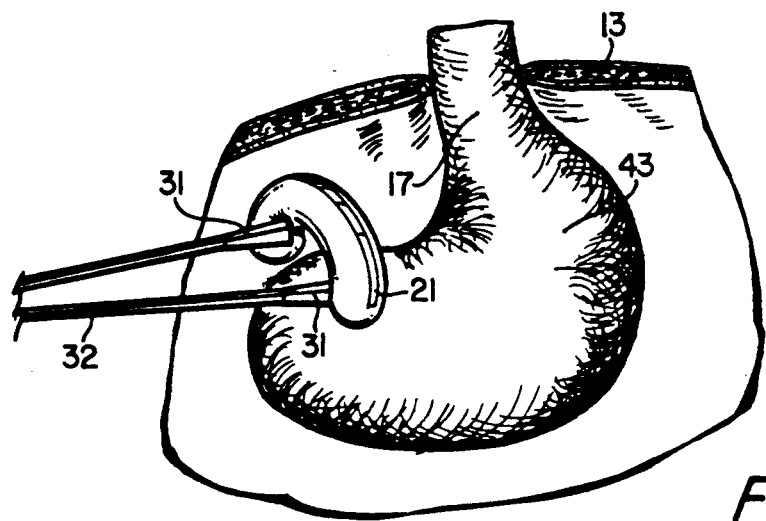
FIG. 4 depicts the temporarily deformed prosthesis of FIGS. 1-3 as it is being positioned around the distal esophagus.
Figure 5:
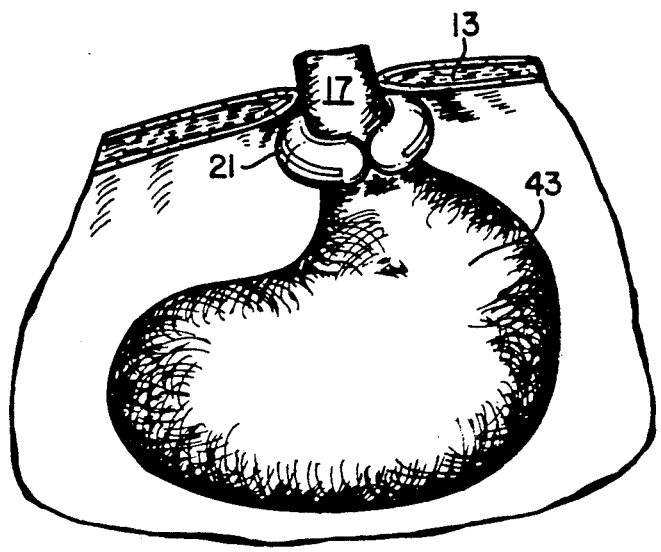
FIG. 5 depicts the prosthesis of FIGS. 1-3 in operative undeformed position around the distal esophagus.
Figure 6:
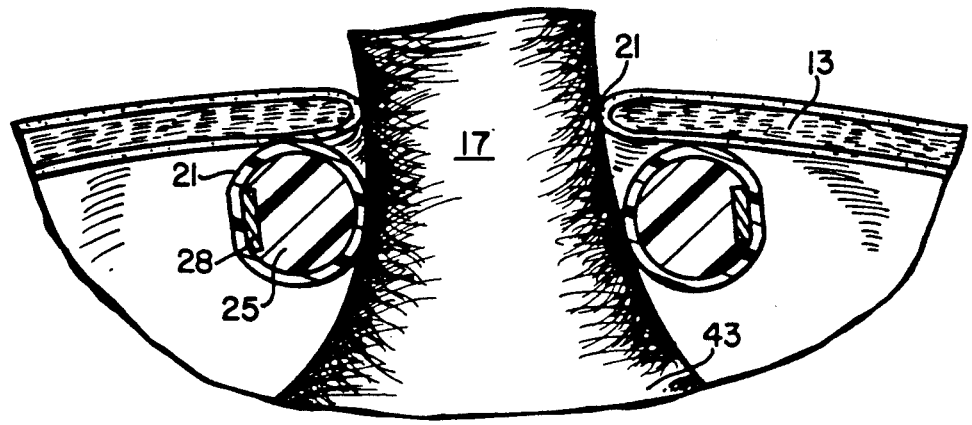
FIG. 6 is a partial sectional view of the prosthesis of FIGS. 1-3 in final, undeformed operative position around the distal esophagus, between the lower surface of the diaphragm muscle and the upper surface of the gastric fundus.

FIGS. 1-3 depict the prosthesis which consists of a generally normally C-shaped cushion member 21, the inside dimensions of which are generally larger than the normal outside dimensions of the distal esophagus (reference character 17 of FIGS. 4, 5 and 6). In a typical prosthesis, the inside dimensions will equal about 3.1 by 2.5 centimeters. In the typical prosthesis the spacing "2" between the ends 29 of the spring 28 will be approximately 1.25 centimeters with a range of from about 1.0 to 1.5 centimeters. The inside diameter of the prosthesis is somewhat larger than the normal outside diameter of the distal esophagus, so as to permit swallowed food, which temporarily forms the distal esophagus to pass through the prosthesis. The soft ends 19 of the cushion member 21 are just touching each other.

The outside dimensions of the C-shaped prosthesis are sized to be substantially larger than the esophageal hiatus (reference character 12 of FIG. 6) and, in a typical prosthesis, the outside dimensions will equal about 6.0 by 7.0 centimeters.

As shown in FIGS. 1-3, the cushion member 21 has a generally circular cross-section and is preferably constructed by filling an outer flexible integument 24 with a fluid 25.

The precise materials for construction of the integument 24 and the fluid 25 of the cushion member 21 are not highly critical so long as they are compatible with body tissues, i.e., do not induce rejection or cause other adverse body reaction. In the presently preferred embodiment of the invention, the integument 24 is a silicone elastomer such as those conventionally employed in forming breast implants, penile implants and the like. The fluid 25 is either a normal saline solution or a hydrogel normally used in penile implants.

A flat band 28 formed of suitable plastic or metallic spring material is enclosed within and secured to the outer wall of the cushion member 21 to urge the cushion member 21 to maintain its normal C-shape. The free ends 29 of the spring 28 are formed with inwardly extending shoulders 29a as shown, which are releasably engageable with the tines of laparoscopic forceps to temporarily deform the cushion member 21 and associated spring 28, as will be described below.

A conventional bladder inflation check valve 27 is provided to permit filling the integument 24 with the fluid 25 through a syringe needle.

In accordance with the presently preferred embodiment of the invention, the spring 28 is preferably formed of a highly radiopaque material to permit fluoroscopic visualization of the prosthesis during and after implantation. According to my present contemplation, the best material for forming this spring element 28 is titanium. Suitable plastics incorporating radiopaque barium compounds which are well known in the art can also be employed. The titanium or barium filled plastic materials provide substantial radiopacity but do not interfere with NMR scans. The cross-sectional dimensions of the spring 28 are chosen to permit the spring to be temporarily deformed for insertion of the prosthesis through a laparoscopic portal without inducing permanent deformation of the spring material. For example, the spring can have a cross-section of about 0.8 centimeters by 0.1 centimeters.

Referring now to FIGS. 4-7, the prosthesis 21 of FIGS. 1-3 is laparoscopically implanted by inserting a laparoscopic portal 41 through the abdominal wall 42 of the patient 45. A laparoscopic optical viewing device 44 of the type well known in the art which provides a video display 45 is also inserted through the abdominal wall 42 in position to view the junction between the distal esophagus 17 and the gastric fundus 43. The peritoneum and a sac of the hiatal hernia (not shown for clarity) are then laparoscopically incised by scissors inserted through the portal 41 and the hernia is reduced by retracting the stomach 43 intra-abdominally by using a laparoscopic forceps 48, inserted through another portal 49. As shown more clearly in FIG. 4, the prosthesis 21 is temporarily deformed by force exerted by the tines 31 which engage the shoulders 29 of the spring member 28 of the prosthesis.

After the deformed prosthesis is inserted through the laparoscopic portal 41 it is positioned (FIG. 4) proximate the distal esophagus 17 and between the diaphragm 13 and the gastric fundus 43. Disengagement of the tines 31 of the emplacement forceps 32 allows the spring 28 to cause the prosthesis to autogenously assume the normal C-shape, encircling the distal esophagus, after which the cushion member of the prosthesis 21 is inflated by fluid injected through bladder valve 29 by means of syringe and needle 33 inserted through the portal 41. Alternatively, the prosthesis 21 is provided which is already filled with fluid prior to insertion through the portal 41; use of a larger portal 41 making it unnecessary to inflate the device prior to inserting it through the portal. In any event the prosthesis 21 is inflated before positioning the prosthesis around the distal esophagus. Additionally, one or more tapes can be provided as disclosed in my previously issued patents to assist the surgeon in passing the device around the esophagus. The entire procedure is conveniently viewed by means of the laparoscopic viewing device 44 during these procedures. When these procedures are completed, the prosthesis 21 will assume the proper operative position as further illustrated in FIG. 6, encircling the distal esophagus 17 and lying between the diaphragm 13 and the gastric fundus 43.

In an alternate embodiment of the invention, my laparoscopic method is practices with the conventional prosthetic device described in my prior U.S. Pat. Nos. 3,875,928, issued April 8, 1975, and 4,271,828 issued June 9, 1981. Such devices may either be proportioned as shown in my previous patents or made somewhat smaller, optionally with provision for deflating and inflating during the procedure.

Further, as depicted in FIG. 8, the laparoscopic method of my invention can also be practiced so as to in placed the prosthesis around the distal esophagus, adjacent to and above the diaphragm through the laparoscopic portal in the thoracic wall.

As further depicted in FIG. 10, these procedures are facilitated by illuminating the esophagus 17 by means a special bougie formed of soft silicone material, approximately 40 to 50 centimeters in length which is inserted intra-orally (see FIG. 7). The bougie contains optic fiber bundles 51 which transmit light from an appropriate high intensity light source (not shown) through the transparent walls 53 of the bougie. The wall 17a of the distal esophagus is sufficiently thin to transmit a substantial portion of the light emitted by the bougie 53 through the walls, facilitating viewing the reduction of the hernia and the emplacement of the prosthesis, in addition to light sources conventionally employed in connection with the optical viewing device 44. Alternatively, the light of a conventional endoscope can be employed with similar, though less desirable effect.

FIG. 9 depicts a pair of forceps 91 which can be effectively employed in the practice in the methods of my invention. Movement of the handles 92 in the direction of the arrows A causes corresponding movement of the tines 93 of the forceps in the direction of the arrows B.

Having now described my invention in such terms as to enable those skilled in the art to understand and practice it without undo experimentation, having disclosed the best mode I presently contemplate for carrying out my invention and having identified the presently preferred embodiments thereof, I claim:

1. A laparoscopically implantable prosthesis for treating esophageal reflux comprising:
   (a) a normally generally C-shaped cushion member, the inside diameter of which is generally larger than the normal outside diameter of the distal esophagus, said normally C-shaped member being temporarily deformable to a shape adapted for inserting said member into a torso cavity through a laparoscopic portal; and (b) shaping spring means formed with said cushion member to normally maintain said cushion member in said C-shape, said shaping spring means being temporarily deformable, with said C-shaped member to said insertable shape.

2. A method for treating gastro esophageal reflux comprising:

(a) inserting a laparoscopic portal through the abdominal wall of a torso cavity;
(b) inserting an optical viewing laparoscope through said wall, positioned to view the distal esophagus;
(c) applying force to temporarily deform a C-shaped prosthesis to an insertable shape;
(d) inserting said temporarily deformed prosthesis through said portal;
(e) positioning said prosthesis around the distal esophagus adjacent the diaphragm.

* * * * *